United States Patent
Robinson

(10) Patent No.: US 6,637,453 B2
(45) Date of Patent: Oct. 28, 2003

(54) DISPOSABLE SURGICAL AND DIAGNOSTIC FLUID CONTROL ISLAND

(75) Inventor: Allan R. Robinson, Saint Anthony, MN (US)

(73) Assignee: Promethean Medical Technologies, Inc., ST. Paul, MN (US)

( * ) Notice: Subject to any disclaimer, the term of this patent is extended or adjusted under 35 U.S.C. 154(b) by 62 days.

(21) Appl. No.: 10/053,141

(22) Filed: Jan. 16, 2002

(65) Prior Publication Data

US 2002/0092563 A1 Jul. 18, 2002

Related U.S. Application Data

(63) Continuation-in-part of application No. 09/562,064, filed on May 1, 2000, now abandoned, which is a continuation-in-part of application No. 09/020,708, filed on Feb. 9, 1998, now Pat. No. 6,568,419.

(51) Int. Cl.$^7$ .......................... A61M 1/00; A61B 19/08; B65D 1/34; F16L 55/07
(52) U.S. Cl. ...................... 137/312; 128/849; 128/855; 137/1; 137/362; 137/561 R; 137/602; 220/571; 141/86; 141/88; 604/356
(58) Field of Search ............................ 4/581, 582, 583; 5/606, 620, 630; 128/849, 853, 855; 137/1, 312, 362, 561 R, 602; 141/86, 88; 184/1.5, 106; 220/571; 222/108; 296/97.23; 604/356, 357

(56) References Cited

U.S. PATENT DOCUMENTS

| | | | | |
|---|---|---|---|---|
| 3,494,356 A | * | 2/1970 | Melges | 128/849 |
| 3,589,365 A | * | 6/1971 | Sejman | 128/849 |
| 4,598,458 A | * | 7/1986 | McAllester | 128/853 |
| 4,679,590 A | * | 7/1987 | Hergenroeder | 137/602 |
| 4,718,653 A | * | 1/1988 | Rothman | 5/606 |
| 4,729,404 A | * | 3/1988 | Hergenroeder | 137/602 |
| 4,890,628 A | * | 1/1990 | Jackson | 128/849 |
| 4,974,604 A | * | 12/1990 | Morris | 128/853 |
| 5,002,069 A | * | 3/1991 | Thompson | 128/849 |
| 5,078,705 A | * | 1/1992 | Edwards et al. | 604/356 |
| 5,199,457 A | * | 4/1993 | Miller | 137/312 |
| 5,287,860 A | * | 2/1994 | Owens | 128/849 |
| 5,349,965 A | * | 9/1994 | McCarver | 128/849 |
| 5,452,739 A | * | 9/1995 | Mustee et al. | 137/312 |
| 5,492,158 A | * | 2/1996 | Haag | 137/312 |
| 5,494,050 A | * | 2/1996 | Reyes | 128/849 |
| 5,503,163 A | * | 4/1996 | Boyd | 128/849 |
| 5,675,854 A | * | 10/1997 | Zibelin | 5/606 |
| 5,709,221 A | * | 1/1998 | Vancaillie et al. | 128/849 |
| 5,738,139 A | * | 4/1998 | DeChard | 137/312 |
| 5,775,869 A | * | 7/1998 | Bishop | 137/312 |

\* cited by examiner

Primary Examiner—George L. Walton
(74) Attorney, Agent, or Firm—Schwegman, Lundberg, Woessner & Kluth, P.A.

(57) ABSTRACT

A device and method for collecting distension media or other fluids discharged during surgical procedures is shown. Also shown is a method for reducing the risk of hyponatremia. The apparatus makes it practical to determine the amount of distension media retained by a patient during hysteroscopic or other surgical procedures, particularly procedures using non-isotonic distension media during monopolar electrosurgery. The apparatus and methods are also useful during a variety of laparoscopic, obstetric, cardiovascular, liposuction, plastic, orthopedic, restorative, and other procedures.

20 Claims, 5 Drawing Sheets

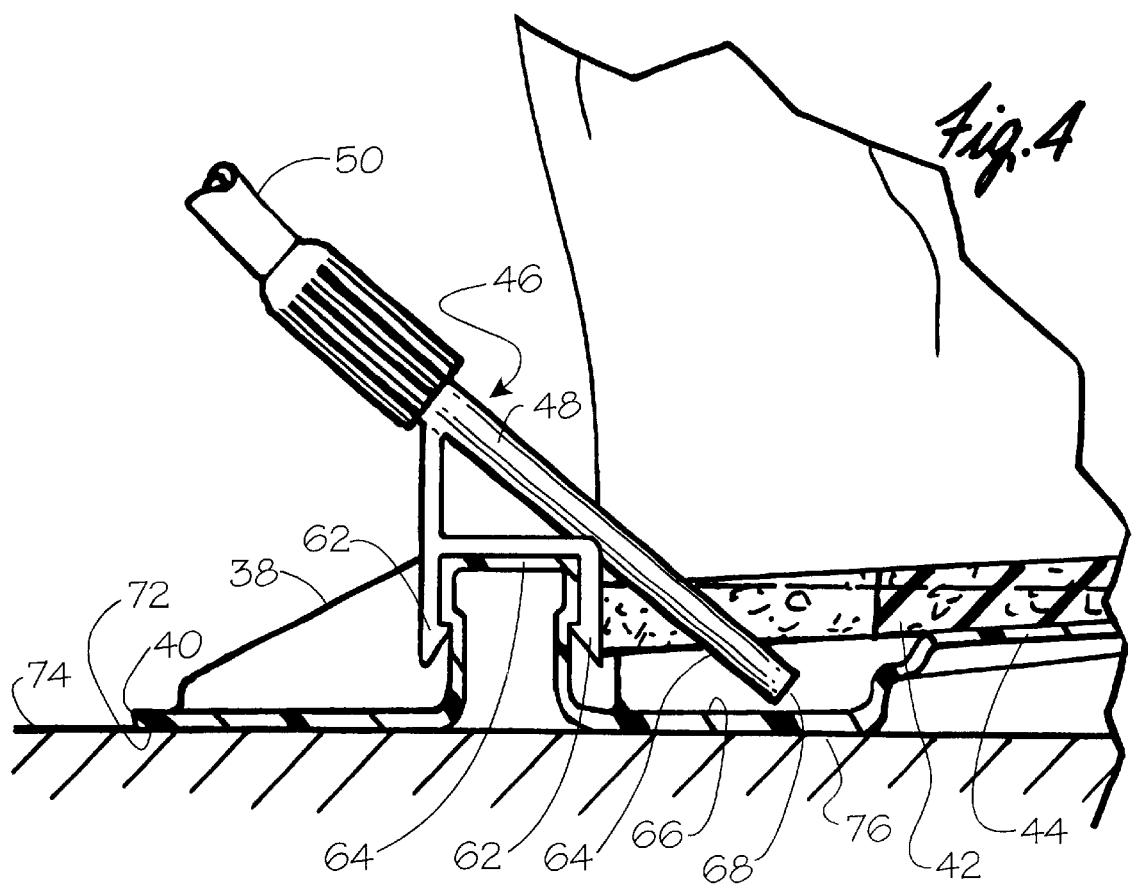
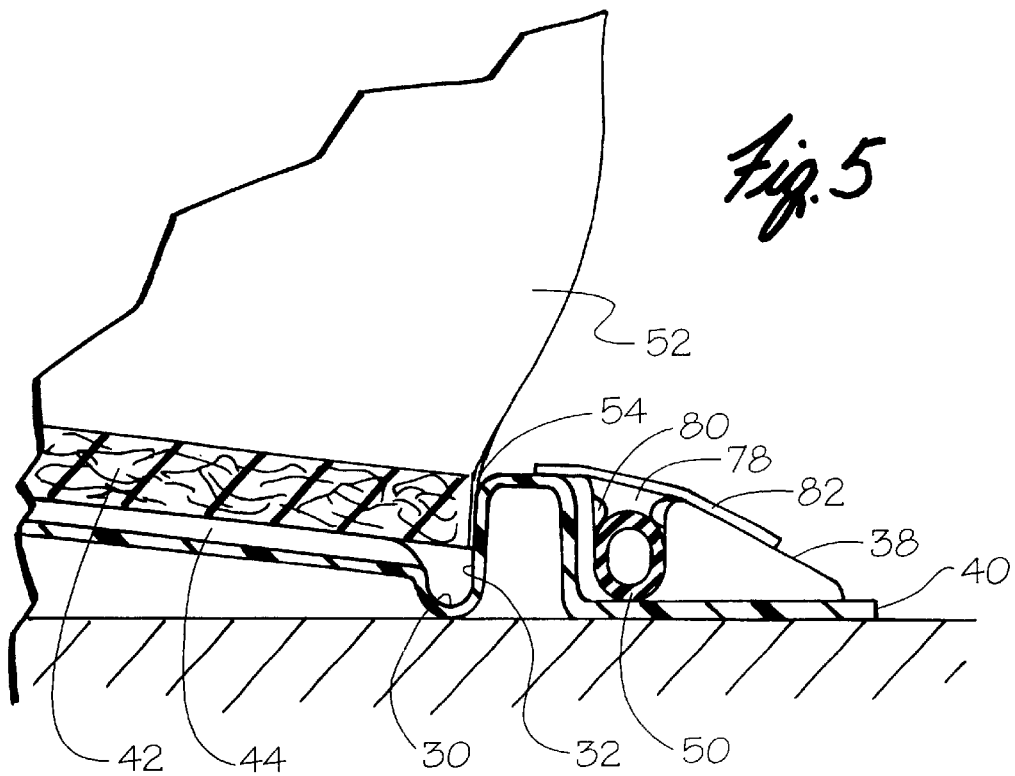

DISPOSABLE SURGICAL AND DIAGNOSTIC FLUID CONTROL ISLAND

REFERENCE TO PREVIOUS APPLICATIONS

This application is a continuation-in-part of my application Ser. No. 09/562,064, filed May 1, 2000, now abandoned, which is a continuation-in-part of application Ser. No. 09/020,708, filed Feb. 9, 1998, now U.S. Pat. No. 6,568,419.

REFERENCE TO GOVERNMENT-SPONSORED RESEARCH

None

TECHNICAL FIELD

The present invention relates to methods and apparatus for control of fluids in work areas. More specifically, the invention relates to methods and disposable apparatus for collecting fluids emanating from a work area. In particular, the present invention provides apparatus and methods for collecting and quantifying the amount of infused and bodily fluids released during surgical procedures, for example during hysteroscopy and urological procedures.

BACKGROUND

A problem affecting the health and safety of a variety of workers is that of providing a safe, non-slippery, dry area upon which the workers can stand. Hospital operating room personnel are routinely required to stand and work in conditions in which the floor is inundated with several liters of distension media, blood, bodily fluids, and other liquids during a single procedure. The abundance of fluids released during surgery is due in part to refinements to diagnostic and surgical equipment, especially the improvements to endoscopic equipment and and the widespread implementation of improved surgical techniques, especially the laparoscopic surgical techniques made possible by improved laparoscopy and other endoscopy tools during recent years.

Fluids dispersed onto operating room tables and floors are a considerable inconvenience to workers, increase the likelihood of contamination, and elevate the potential for spread of infectious disease. Others have attempted to reduce the dangers of slippery floors and the like. For example, U.S. Pat. No. 4,635,913, issued Jan. 13, 1987; U.S. Pat. No. 4,718,653, issued Jan. 12, 1988; and U.S. Pat. No. 4,811,937, issued Mar. 14, 1989, Rothman disclosed a series of Portable Surgical Drainage Platforms. The inventions he developed could assist surgeons and other surgical staff by supporting the personnel on grating and removing liquid that falls through the grating. The platforms are, however, rather heavy and are also difficult to sterilize, especially in the limited amount of time that may be available between surgeries.

LaRooka received U.S. Pat. No. 4,243,214 on Jan. 6, 1981, for her Irrigation-Debridement-Repair Caddy. That disclosure is directed to an apparatus that can be placed under an extremity of a person during a surgical procedure. The Irrigation-Debridement-Repair Caddy is designed to collect some of the irrigation distension fluid and excised tissue that would otherwise drip onto the floor and collect the fluid in a closeable bottle for eventual disposal.

Other devices such as the AquaVac mat marketed by Arthroplastics of P.O. Box 332 Chagrin Falls, Ohio 44022 appear to be directed primarily toward removing water from floors rather than quantifying the amount of fluid received from a patient in order to determine whether the patient's condition is satisfactory.

Endoscopic diagnostic and surgical procedures often use some type of distension fluid (usually a clear liquid) infused into the region where the procedure is being conducted to allow the surgeon to see the affected tissue much more clearly than would otherwise be possible. In addition, the distension fluid can separate and stabilize the tissue to improve surgical precision and reduce the time required to carry out procedures. Any of several liquid distension media may be used during diagnostic and surgical endoscopic procedures. Ringer's solution and 0.9% saline solution may be used during diagnostic examination or laser surgery but are unsuitable when electrosurgery or electrocautery procedures might be undertaken. Non-electrolytic distension media such as 1.5% glycine, mannitol, or sorbitol solutions, among others, can be used for electrosurgery or laser surgery. Since all of the liquid distension media formulations are selectable and equivalent for the purposes of this disclosure, they may be referred to indistinguishably as distending medium, distending media, distension medium, distension media, whether singular or plural.

Hysteroscopic, urologic, and some other surgical patients are usually infused with a distension medium. If non-electrolytic distension medium enters the circulatory system, it can cause blood dilution and lowered ionic strength. Swelling can result as tissue takes up water to restore the correct blood osmolarity. A patient can suffer serious, or even fatal, complications if too much distension media is absorbed. The variety of symptoms associated with the absorption of large volumes of distension media is called "post-TURP syndrome" by urologists. Symptoms include bradycardia and hypertension followed by hypotension, nausea, vomiting, headache, visual disturbances, agitation, confusion, and lethargy; the symptoms result from hypervolemia, dilutional hyponatremia and decreased osmolarity. Without treatment, possible results include seizures, coma, cardiovascular collapse, and death.

The amount of distension media that a patient can absorb without intolerably dangerous adverse effects is related in non-intuitive ways to various individual physical, chemical, and other factors. The preoperative nurse will estimate the volume of distension media that each patient is reasonably expected to absorb without complications by factoring the patient's age, weight, fitness, hormonal balance, the formulation of the distension media, the procedure being performed, and a host of other variables before the patient arrives in the operating room. Unfortunately, the full utility of that estimate can be realized only if the amount of fluid actually retained by the patient can be timely determined with sufficient accuracy while the procedure is being performed. Some reports suggest that most patients can absorb approximately one liter without life-threatening effects. However, fluid overload with very serious complications caused by absorption of 0.8 liters of distension medium has been reported.

The quantity of distending medium absorbed by a patient naturally increases with the length of time required to perform the procedure. Hospitals, surgeons, and patients normally seek to conclude the surgery as quickly as possible for good reasons. Other things being equal, the less time required to perform a surgery, the better the expected outcome and the quicker the patient is expected to recover.

Instilled fluids are taken up by the patient more rapidly during some procedures, compared to others. Sometimes distension fluids are absorbed so rapidly that the surgeon may not have enough time to address and correct all of the problems and complexities discovered during the surgery. In such instances, it might be necessary to terminate a procedure when only a few additional minutes of the surgeon's time would be sufficient to complete the process as desired. That is a very undesirable situation because patients in those cases must be allowed to recover in the hospital for several days and then, often in a weakened condition, again be prepared, anesthetized, and the surgery resumed. Because those additional risks are widely recognized, as is the risk of continuing a surgery when a patient may, or may not, be in danger from excessive absorption of distension media fluids, the surgeon, lacking accurate information, is forced to make a decision that can easily be criticized in hindsight. It is necessary to expand some tissues, for example the uterus, in order to adequately view the structures for diagnosis and surgery.

Based on these factors, it is easy to understand that surgeons, hospitals, and their patients would be greatly assisted by more accurate knowledge of the amount of distending medium retained by surgical patients. Although instilled distending medium may accumulate in the abdomen or the patients extremities, the greatest concern is for accumulation and absorption of distension medium during surgeries in which severed veins are exposed to pressurized distending medium. Hysteroscopic and, to a lesser extent, urologic procedures performed using monopolar electrosurgery inherently give rise to conditions that can quickly lead to dangerous complications if any member of the surgical team is unable to maintain a vigilant lookout for the onset of hyponatremia.

The hazards of hyponatremia are widely recognized by workers throughout the fields of obstetrics and gynecology. Medical literature has many excellent publications addressing the problem in varying breadth and depth which led to the publication of "Hysteroscopic Fluid Monitoring Guidelines" by the Ad Hoc Committee on Hysteroscopic Fluid Guidelines of the American Association of Gynecologic Laparoscopists in the Journal of the American Association of Gynecologic Laparoscopists, Vol. 7, No. 1, in February, 2000. Those guidelines state that "mechanical monitoring is highly desirable since it removes the human factor in measuring fluid deficit, allows for early warning of excessive intravasation by real time totals, and indicates the rapidity with which the loss is occurring. If mechanical monitoring is not available, an operating room person should be dedicated to frequent measurements of intake, output, and deficit."

A good overview explaining the subject and the causation of the potential harms is presented by Donna Morrison, R.N. in her article "Management of Hysteroscopic Surgery Complications," J. Assoc. of Operating Room Nurses, vol. 69, no. 1, January 1999, pp. 194–209. Morrison explains that dilutional hyponatremia is a complication of hysteroscopic surgery that is associated with intravasation of a low viscosity non-electrolytic distension media. Women are more likely than men to suffer dilutional hyponatremia, and premenopausal women are 26 times more likely than postmenopausal women to encounter hyponatremia. Pre-menopausal women are at greatest risk, then, usually as the result of hysteroscopic procedures; the same considerations are, however, important in urologic, and perhaps other procedures that may be undertaken on either male or female patients. For the convenience of the reader, it is to be understood that references to hysteroscopy and hysteroscopic procedures are intended to include for the purposes of this disclosure, urology, urologic, and urological procedures, and any other type of surgical procedure that exposes the patient to risk of hyponatremia or in which it would be helpful to know the volume of instilled fluid retained by a patient.

Some types of non-electrolytic distension media (such as sorbitol and 1.50% glycine) used in monopolar electrosurgery have lower osmotic potential, or tonicity, than the patient's tissues, serum, and intercellular fluids. For that reason, the distension media is absorbed fairly quickly by the tissues surrounding the surgical site. Not only is the distension media absorbed quickly by osmosis, the fluid is supplied under pressure in order to distend the area where the surgery is being performed to enable the surgeon to repair damaged tissue with greater speed and precision. The fluid pressure applied to distend the surgical area can exceed the patient's venous pressure thereby actively forcing distension media into blood veins that are cut or broken in the course of the surgery. Free water and distension media can enter the vascular system through blood vessels and sinuses opened as the integrity of the endometrial lining or other tissue is interrupted during surgery. Some distension media formulations will bring additional diluent water, beyond the volume of the distension media itself, into the blood stream. Since the risk posed by that effect is some function of the volume of distension media taken up by the patient, it can be seen why it is highly desirable to be able to quantify the amount of distension media retained by the patient.

Other types of non-electrolytic distension media, such as 5% mannitol have diuretic properties. It may, however, cause hyponatremia.

Efforts to cauterize exposed vasculature are maintained throughout the surgeries, however the process is not always instantaneous, and some distension media will be forced into the patient's circulatory system as a result. The duration of the surgery must be limited for that reason, even under the best of circumstances. As a practical matter, undetected damage to vessels or other tissue exposed to the pressurized distension media will sometimes be present, vasculature thought to have been cauterized may subsequently begin to admit distension media, or other sub-optimal conditions may develop. It is to be understood that before surgery commences almost all patients who undergo laparoscopic urological and gynecological surgeries have sub-optimal conditions with tissue damage that could increase the likelihood that distension media will be retained. Any event or condition that increases the patient's uptake of distension media necessarily shortens the permissible duration of the surgical procedure.

If that were the extent of the problem, a patient in that situation might merely need to endure a period of uncomfortable puffiness. However, the brain, like the rest of the patient's tissue, seeks to balance the ionic strength of the diluted blood by removing water from the blood and adding that water to the brain tissue. The skull provides scant room for the brain to expand as it swells from the added water; extreme pressure can build fairly quickly. Brain stem herniation can develop as the brain expands attempting to equalize interstitial and intervascular osmotic pressures. This condition, hyponatremic encephalopathy, has high morbidity and mortality rates and may result if dilutional hyponatremia is not recognized at its onset and treated promptly. The "Hysterocopic Fluid Monitoring Guidelines" referred to above recommend that if fluid intravasation reaches 750 ml, "completion of the case should be planned. If fluid intravasation reaches approximately 1500 ml of non-electrolyte or 2500 ml normal saline, the case should be brought to a conclusion, electrolytes assessed, administration of diuretics considered, and further diagnostic and therapeutic intervention begun as indicated." The guidelines require that "both anesthesiologist and surgeon be made aware of the fluid deficit frequently" during every procedure. Tracking the amount of distension media administered to the patient and collecting and measuring all of the fluid returned from the patient is the quickest way to detect possible intravasation caused dilutional hyponatremia.

To that end, surgeons often request the operating room personnel to report the amount of fluid that has been introduced into and received from the patient. Fluid limits are normally fixed between 500 ml and 1,500 ml., and surgery time is frequently limited to one hour. Unfortunately, it is difficult to reliably measure the volume of distension media received from the patient using traditional methods and equipment. Likewise, it is difficult to measure the volume of fluid infused with traditional methods and equipment.

Operating room personnel will know with certainty the number of 3 liter bags of distension media that have been infused at any particular time. Beyond that, there has been little certainty available. To estimate the amount remaining in a partially used 3 liter container of distension media, it is usually necessary to remove the bag from the pressurizing cuff or collar in which it is located during use. Of course, removing the pressurizing collar halts the flow of distension media to the location of the surgery which can quickly interrupt the conduct of the procedure. Once the uncalibrated, shapeless 3 liter bag is visible, operating room personnel would then estimate (i.e. guess at) the amount remaining in it. The amount of infusion fluid discharged from the hysteroscope outflow would normally be collected, and therefore measurable. Careful draping can direct some of the returned fluid into kick buckets, but some is likely to disperse onto the operating room floor, the table, and into pads or towels. The difference between the amount of fluid introduced and the amount of fluid collected or dispersed onto the operating table and floor gives some estimation of the amount of fluids remaining in the patient. Such estimates are crude approximations at best, and are generally recognized as such by those who make and use them.

A cross check may be provided by measuring serum sodium concentration during the surgery both periodically and whenever intravasation is suspected. It is sometimes necessary to halt the surgery while awaiting serum sodium test results.

If the surgical team discovers that intravasation has occurred, the situation is normally treated as an emergency requiring the surgeon to halt the procedure as soon as it is safe to do so. Electrolytes, oxygen, and other treatments would be administered as quickly as possible.

It is readily appreciated that the consequences of underestimating the amount of infused fluid taken up by the patient can include morbidity and mortality. Overestimating the amount of fluid taken up by the patient can result in premature termination of surgery and can instigate an emergency response that imposes additional risk upon the patient.

In an effort to determine the reliability of the estimates of fluid balance that operating room personnel make, a preliminary test was conducted by one hospital to evaluate the accuracy of visual estimates of fluid volumes experimentally. Four experienced operating room nurses were each asked to visually estimate fluid volumes under nineteen different conditions: the amount of distension media remaining in ten different 3 liter bags; the amount of fluid received in four different kick buckets; and the volume of fluid present on five different operating room floors. The results of the experiment are presented in Table 1. Although the individuals were experienced, trained, and capable in their fields, their estimates of fluid volumes deviated from the actual amounts sufficiently to risk premature cessation of a surgical procedure in most instances. Participants underestimated the amount of fluid present regularly. Out of 76 estimates 74 were less than, and only two exceeded, the actual liquid volume. The errors are additive, and effect of the cumulative errors is that, even if only the best estimate from each trial is considered, in more than 750% of the cases, a recommendation to halt the surgery is indicated by these estimates, even if absolutely no distension media had been retained by the patient.

In the effort to more accurately evaluate the amount of distension media returned by the patient, surgical drapes may be arranged to direct the returned fluid to buckets positioned on the floor. It can be necessary to halt the surgery while the unsterile contents of the buckets are measured. But, as can be seen from studying Table 1, the estimation errors for the amounts of fluid on the operating table and on the floor can be so large that there is little value in knowing the volume of fluid accumulated in the kick buckets.

What is needed is a practical way to collect fluids returned from a patient during hysteroscopic surgical procedures.

Also needed is a way to measure the volume of fluids returned from a patient during hysteroscopic surgery.

Another need is a practical way to collect fluids returned from a patient during urological surgical procedures.

An additional need is for a way to measure the volume of fluids returned from a patient during urological surgery.

A further need is for a way to collect and contain fluids discharged by a patient during childbirth.

Another need is for a way to collect and remove fluids received from a patient during orthopedic surgeries.

Another need is for a disposable surgical and diagnostic fluid control system having an integral drape.

Also needed is a fluid control system having pre-formed resilient dams to route fluids toward a collection point.

Yet another need is for a fluid control system having integral channels for routing suction tubing.

Yet another need is for apparatus making it possible to quickly determine the difference between the amount of distension media that has been infused into the patient and the amount of distension media that has been returned from the patient.

SUMMARY

The present disclosure meets the many previously unfulfilled needs that are part of the background leading to the development of the various embodiments according to the present disclosure.

Previously known methods and apparatus have been unable to overcome the various problems encountered by people who work in areas where wet floors are routinely encountered. In hospital operating rooms and delivery rooms, for example, the method for controlling wet floor problems is often merely to scatter disposable absorbent blankets, pads, or mats on the floor. Following surgery, the absorbent material may be weighed to measure the amount of fluid lost by the patient during the procedure. Typical absorbent blankets are made of materials similar to those used to make disposable diapers. It may readily be appreciated that standing, walking, and working with several pieces of that type of material disintegrating on the floor surface is difficult, at best. Unfortunately, those activities are especially difficult under actual conditions because the considerable activity during a surgical procedure tends to bunch up the absorbent materials. It can be appreciated that these circumstances are not conducive to quickly obtaining accurate information about the quantity of distension media that may have been introduced into a patient's vasculature.

What is needed, then, is a disposable surgical and diagnostic fluid control island placeable on an operating room floor for selectably collecting, retaining and draining fluids received from patients during surgery comprising a generally broad, shallow, impermeable vessel-forming base having a peripherally floor-contacting, undersurface portion, an upper surface portion with a raised center, a multiplicity of sloping channels extending downward from the raised center toward a lower peripheral channel at the base of a generally vertical peripheral wall disposed between a fluid-contacting central portion and a distal peripheral skirt, a generally beveled upper skirt surface extending between the top of the generally vertical peripheral wall and a distal base edge proximate the floor, a generally non-absorbent splash pad disposed within the fluid-contacting central portion and supported by ribs above the sloping channels and extending proximal to the raised peripheral wall, and means for connecting fluid-removing suction tubing proximate the lower peripheral channel.

It is to be understood that, for the purposes of this disclosure, an operating room floor can be any surface located below a patient who is undergoing any diagnostic, childbirth, or surgical procedure, and includes, among other examples, ambulances, vehicles or all types, including aircraft and waterborne vessels. It is the intent that the invention be useable below a patient for gravity collection of fluids that are released during surgical and diagnostic procedures and that any surface capable of supporting an embodiment of the invention is either a floor or equivalent to a floor.

Accordingly, it is an object of the invention to provide a practical apparatus to collect and quantify the volume of fluids returned from a patient during hysteroscopic, urological, orthopedic, and other surgical procedures.

Another object of the invention is to provide apparatus and method to collect and contain fluids discharged by a patient during childbirth.

A further object is to provide a disposable surgical and diagnostic fluid control system having an integral drape.

Another object is to provide a fluid control system having pre-formed resilient dams to route fluids toward a collection point.

Yet a further objective is to provide a fluid control system having integral channels for routing suction tubing.

Yet another object is to provide apparatus making it possible to quickly determine the difference between the amount of distension media that has been infused into the patient and the amount of distension media that has been returned from the patient.

It is possible to fabricate the splash-arresting mesh or pad in specific colors to accomplish additional purposes. For example, using a white mesh can make it easier for operating room personnel to determine whether blood is escaping from the patient. It may also be possible to coat the mesh with indicator dyes that would alert operating room personnel to the presence of substances of concern.

Embodiments of the present disclosure meet these needs, and more, by solving the long-recognized problem of containing and removing fluids received from surgery patients so that the volumes of the fluids can be measured and liquid dispersal throughout the working area can be minimized. The present disclosure teaches a disposable, fluid containing and draining vessel, or base, formed of impermeable material having channels that route fluids impinging upon the base to fluid evacuation wells, means for connecting suction proximate the evacuation wells, and a splash-arresting pad that covers the wetted area of the base. The splash control pad may be made of woven or non-woven textile, a macro-porous open-celled foam or other material, preferably a material that does not retain fluids.

The base may be made of any impermeable material, for example recycled plastic soda containers. The base may also be made of impermeable sheet foam, metal foil, coated paper, or other materials. Sheet stock made from recycled beverage containers is widely available in thicknesses of 25 to 30 mil which can be readily vacuum-formed to produce a functional base having good shape-retention characteristics. It is desirable to have the overall base constructed in a low modified conical shape having the central wetted area covered by the splash pad and the drape surrounding the splash pad by approximately 270 degrees. The base is generally tapered from the apex toward the floor with a radial array of ribs that support the splash pad above hollowed-out downwardly-sloping channels formed between the ribs.

A generally circular diagnostic and surgical fluid control system base may be made in any desired size. If, for example only, and not by way of limitation, it is desired to have a radius of six inches for the central, wetted portion, and a peripheral skirt annular dimension of 2½ inches, the overall diameter will be seventeen inches and may have an apex of ¾ inch above the floor or other equivalent support surface. A fluid conducting channel may be formed at the circumference (or periphery) of the fluid capturing wetted area and radially (or medially) inside the skirt for fluid communication between the fluid evacuation wells and a suction port which may optionally be affixed at any of several locations as may be convenient if the base is level and to the lowest one if the base is slanted. The floor or other supporting surface can contact the undersurface of the material from which the base is constructed at the undersurface portion of the bottom of the peripheral channel and at the undersurface portion of the bottoms of the fluid evacuation wells in addition to the peripheral outer edge of the skirt. This configuration allows fluids to flow quickly by gravity through the splash-preventing pad, or mesh, down sloping channels to a relatively narrow peripheral channel that has low volume and into the evacuation wells. Although fluids can be extracted from all of the evacuation wells, it is generally sufficient to evacuate the fluids from one well using house vacuum where the fluids are collected in vacuum canisters of any now known or later-developed type.

Suction tubing management may be provided by a tubing guide channel formed in the skirt. Walls of the tubing guide channel may have protrusions to retain the tubing after it has been placed into the channel. An optional tubing retainer plate or flap may be formed of the same stock as the base, or from different material, and affixed to the base at one or more locations in any manner, for example, by sonic welding, adhesive, solvent welding, mechanical fasteners, or heat sealing, to keep the suction tubing in the desired location. The tubing guide channel may conveniently go 360 degrees which can simplify assembly by removing any necessity for orientation of that element with others.

Conventional-style polyethylene surgical draping material may optionally be affixed to the base so that fluids are reliably conveyed to the base for removal. The drape may also be fitted with an optional tissue and debris collection pocket having a liquid-permeable screen or mesh and a drain opening below the screen. Optional integral resilient fluid containment elements may be formed in the drape at the portion between the patient and the operating table by folding portions of the sides of the drape and the end over a somewhat resilient member such as urethane foam rod or strip, macro-porous open-celled foam, non-woven mesh, sponge, or innumerable other materials capable of elevating the folded portion of the drape material slightly above the table to prevent fluids from flowing under the patient or over the side of the operating table. The drape assembly may optionally be sterile or sterilizable or non-sterile.

The base is not intended to support a person, however, it should not be harmed if a person steps or stands on it. A resilient foam post may be affixed to the underside of the apex to prevent the cone pitch from inverting as the result of someone stepping on the base. With a diameter of approximately 17 inches, the fluid control island is small enough to fit between the feet of the surgeon and to also be easily relocated if desired. Although the base is depicted as round, it is to be understood that other shapes are equivalent.

When the procedure is finished, suction may be disconnected, the drape removed from beneath the patient, and the drape, base and any tubing placed in a bag for proper disposal, usually by incineration. With proper suction, fluid residence time in the base is very low, and the latent volume retained in the splash pad, the drape, and the base is usually less than approximately 75 ml.

Materials preferred for the product are inexpensive and lightweight so that the fluid control island may be shipped, stored, and handled easily by personnel who have no special training, physical abilities or equipment. It is also preferred that the splash pad be inexpensive so that the fluid control island can be disposed of destructively to reduce the potential for environmental and health hazards that might result from attempts to clean and re-use the components. It is also preferred that the product has good shelf life. Other desirable assembly material characteristics include: that it is non-slippery when wet, that it remains flat on the floor surface while the fluid control island is in use, that liquids may be readily removed from the base and splash pad for recovery or analysis, that it be easily bonded to the drape material, that it does not cause allergic reactions, and that it does not create difficult disposal problems.

The splash control pad may have a mesh thickness of about ¼" to ¾." The conical drainage slope causes the liquid to flow from the raised center of the wetted area radially or outwardly through sloping channels toward the peripheral fluid channel and the evacuation wells where suction removes the fluid to containers. Very little fluid remains in the vessel or the splash pad. Evacuation of the vessel can easily be accomplished with either a vacuum source and fluid collection canisters or with use of a pump capable of pumping the specific liquids that a particular vessel collects. Such a fluid control island vessel, with the support mat in place, can contain a substantial volume of fluids giving the system a surge capacity that makes it possible to use a relatively low rate of fluid removal with an inexpensive removal system, whether vacuum operated or pumped directly, yet still have sufficient capacity to collect and remove all the fluids collected in the vessel during a procedure. A base having a 17" diameter and a depth of approximately ¾" has sufficient surge capacity to handle most vaginal birth cases without overload.

It is believed that the integration of surgical drapes with the fluid control apparatus can enable gynecological and urological surgeons to use general operating rooms rather than being restricted to specially equipped operating rooms. This advantage could make it possible for patients and physicians to obtain these surgical services at many additional hospitals and clinics.

By collecting substantially all of the fluid received from a patient during hysteroscopic and urological procedures, it is possible to know with previously unobtainable accuracy how much distension media is discharged from the patient. It is also necessary to determine the amount of fluid introduced to the patient to compute the retained volume. In a further development of the invention, the container (usually a 3 liter flexible plastic bag) of distension media, together with any pressurizing device for forcing the fluid out of the container, is suspended from a scale that allows surgical personnel to determine the difference between the initial weight and the weight at any subsequent time. Conversion of the weight difference is straightforward since the density of the distension media is known. The fluid received from the patient can be drawn into collection canisters by house vacuum where the volume can be conveniently measured directly using calibrated containers.

Alternatively, collected fluid can be weighed using any of a variety of techniques to establish the differential between the weight of the fluids supplied to the surgical site and the weight of the fluids recovered using an embodiment according to this disclosure in addition to those returned from any other source (such as hysteroscope bypass or flushing). The fluid collected by the fluid control island may also be pumped to the collection containers. It may also be possible to weigh the distension media supply and the returned fluids collected on the same scale to achieve an accurate measure of fluid remaining in the patient in real time. Another alternative method is to measure the amounts of fluid introduced into and received from the patient with mass flow meters and compute the difference electronically to inform the surgical team of the amount of fluid retained by the patient.

BRIEF DESCRIPTION OF THE DRAWINGS

FIG. 4 is a sectional detail of the disposable surgical and diagnostic fluid control system embodiment of FIG. 3 showing the suction port and connection in greater detail.

FIG. 5 is a sectional detail of the disposable surgical and diagnostic fluid control system embodiment of FIG. 3 showing the suction tubing installed in the tubing guide channel.

DETAILED DESCRIPTION OF THE PREFERRED EMBODIMENT

The construction of a fluid control island for diagnostic and surgical procedures may be understood viewing the accompanying FIG. 1 through FIG. 6, particularly in view of my co-pending patent applications, Ser. Nos. 09/020,708, and 09/562,064, which are incorporated herein by reference.

Figure 1:
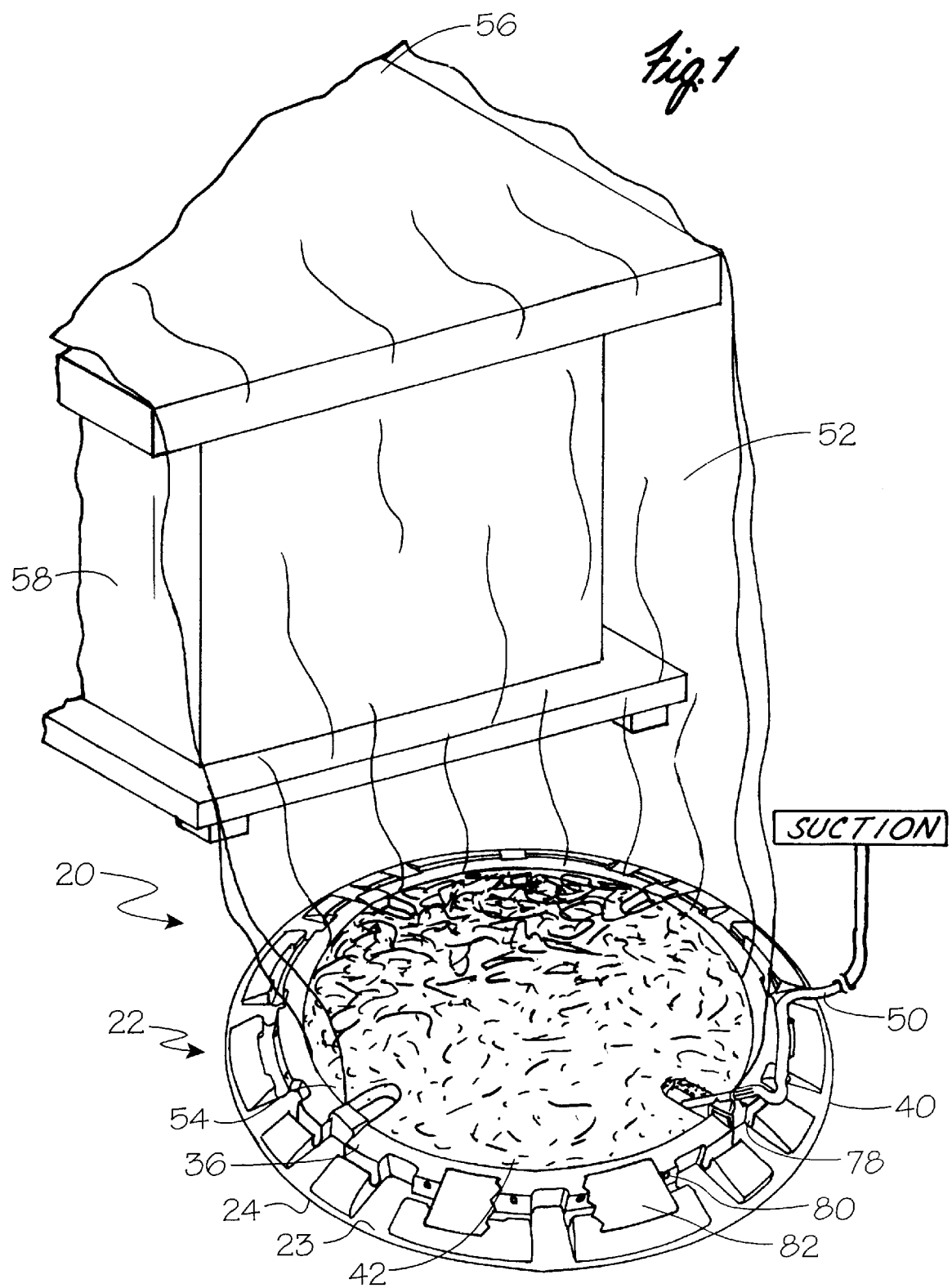
FIG. 1 is a perspective view showing a disposable surgical and diagnostic fluid control system with attached surgical drape and vacuum operated fluid removal provision.

FIG. 1 shows, in perspective, a disposable surgical and diagnostic fluid control island 20 placeable on an operating room floor for selectably collecting, retaining and draining fluids received from patients during surgery comprising a generally broad, shallow, impermeable vessel-forming base 22. The base 22 may be formed from any material by stamping, injection molding, vacuum forming, rotary molding, blow molding, and other techniques to produce a generally horizontal part with an upper surface 23 and a peripherally floor-contacting, undersurface 24.

Figure 2:
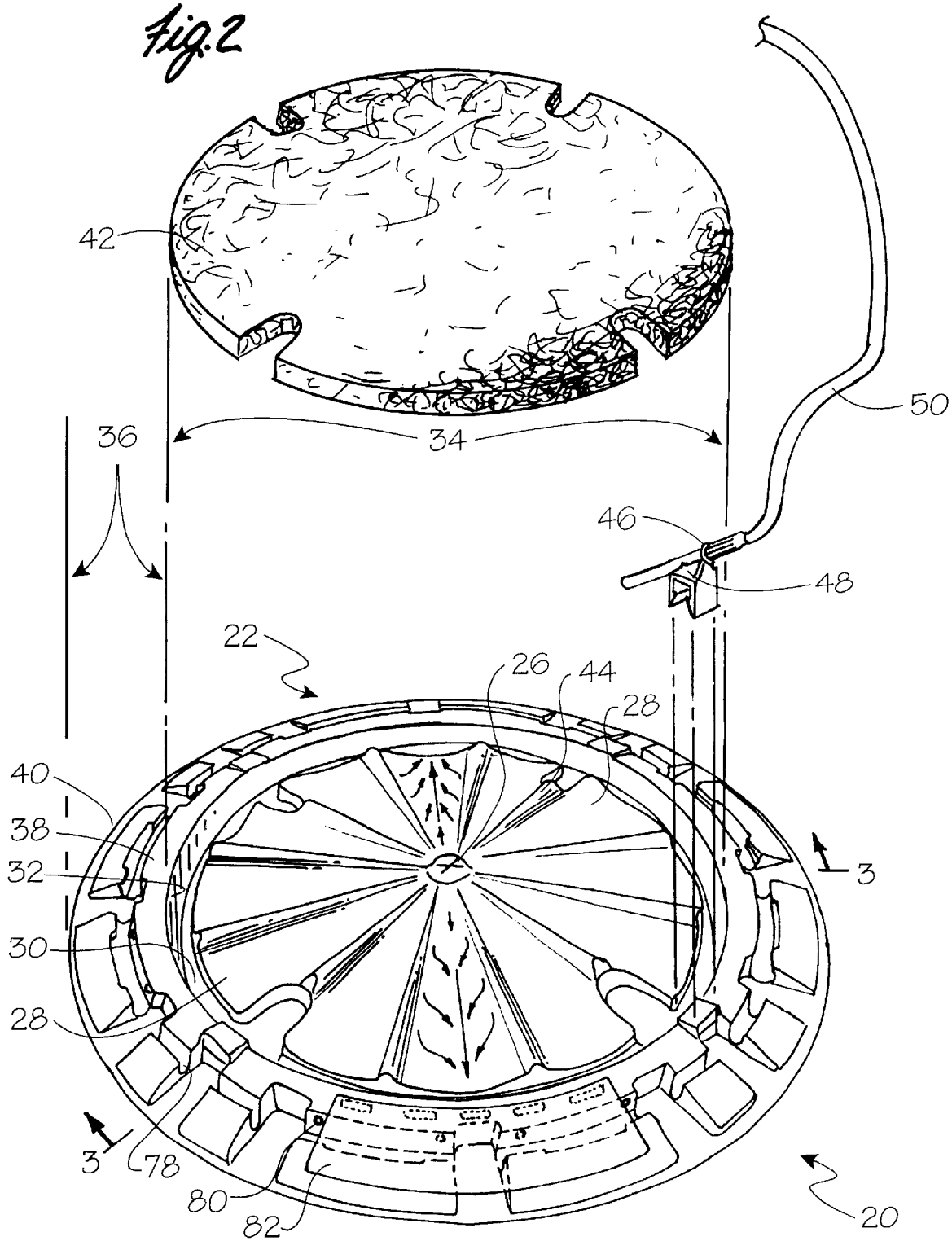
FIG. 2 is an exploded view of the disposable surgical and diagnostic fluid control system shown in FIG. 1.

As can be more clearly viewed in FIG. 2 the base 22 may be formed with a raised center 26 having sloping channels 28 sloping radially downward toward a lower peripheral channel 30 at the base of a generally vertical peripheral wall 32. The vertical peripheral wall 32 divides the upper surface 23 into two regions because it is disposed between a fluid-contacting central portion 34 and a radially outwardly, or distally, disposed skirt 36. A generally beveled upper skirt surface 38 extends between the top of the generally vertical peripheral wall 32 and a distal base edge 40 proximate the floor. A generally non-absorbent splash pad 42 disposed within the fluid-contacting central portion and supported by ribs 44 above the radial sloping channels 28 and extending proximal to the vertical peripheral wall 32, and means 46 for connecting 48 fluid-removing suction tubing 50 proximate the lower peripheral channel 30. The sloping channels 28 need not be radial, but could be downwardly sloping from the center toward the periphery of any shape. Retention of water is minimized by making the sloping channels 28 with conical, or scalloped, cross-sectional curvature (viewing in the direction of fluid flow) so that fluids impinging on the fluid-contacting central portion 34 is provided a fairly steep path down which to flow and by which droplets may converge to more rapidly flow to the lower peripheral channel 30 for removal.

Although a base 22 mating tubing connector 48 is illustrated, it is to be understood that other means for connecting 46 suction tubing 50 proximate the fluid channel 30 may be used equivalently. Examples of other potential means for connecting the suction tubing 50 include bulkhead connectors, adhesives, mechanical fasteners, and all other commercially available tubing connection devices. In some cases, it may be possible to insert suction tubing 50 directly into the peripheral fluid channel 30 below the splash pad 42.

Figure 6:
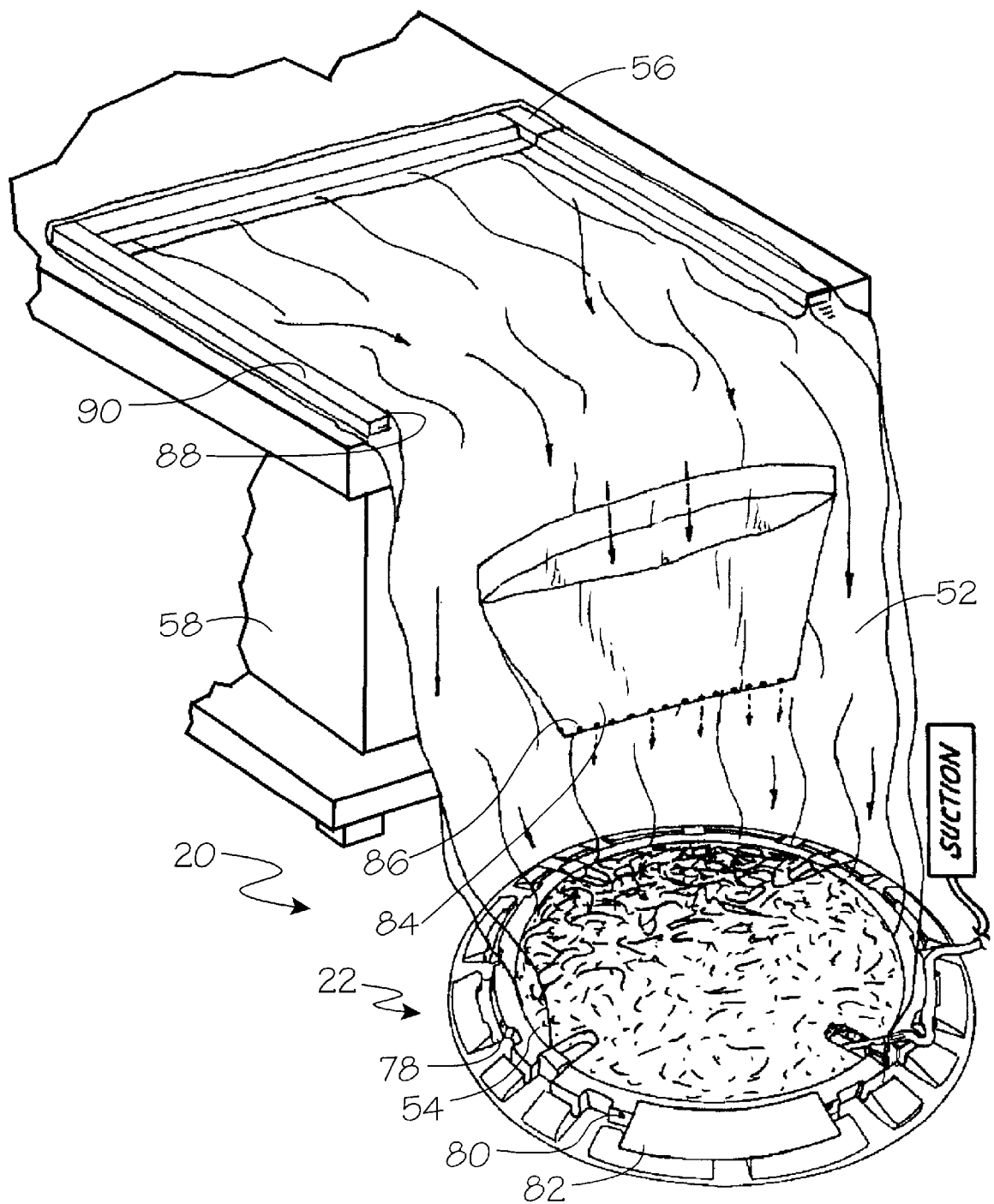
FIG. 6 is a perspective view of an alternative embodiment of the disposable surgical and diagnostic fluid control system of FIG. 1 further depicting optional resilient dams formed integrally with the drape and an optional tissue and debris collection pouch with drain.

An option that may be included is an elongated drape 52 lower end 54 affixed to the base 22 proximate the peripheral wall and an elongated drape upper end 56, shown in FIG. 1 and FIG. 6, may be disposed upon an operating table 58 for fluid communication between a patient and the base 22.

Figure 3:
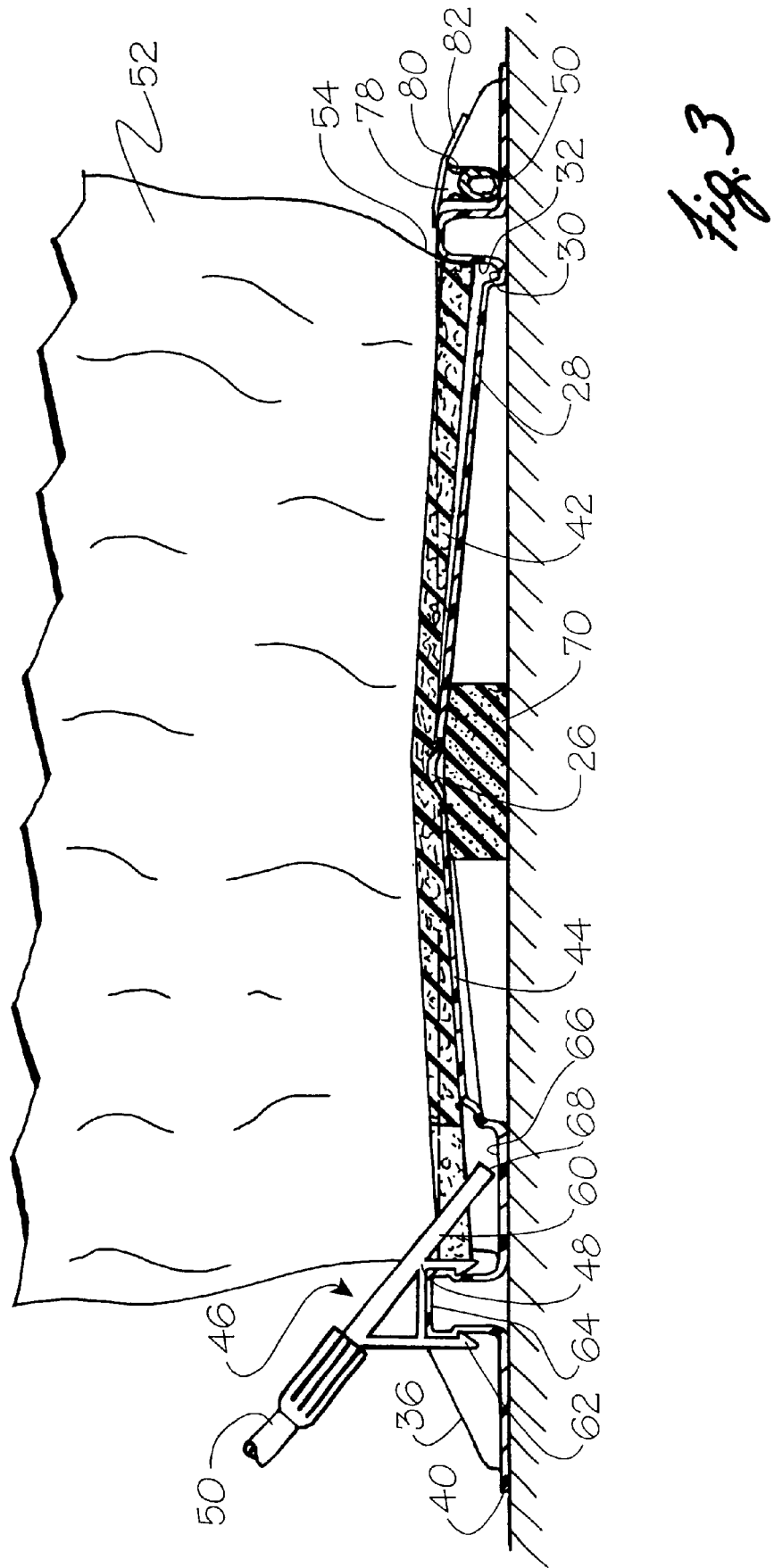
FIG. 3 shows two radial sections of the disposable surgical and diagnostic fluid control system of FIG. 2 taken at 3—3.

Viewing FIG. 3 shows two radial sections of the disposable surgical and diagnostic fluid control island 20 of FIG. 2 taken at 3—3. The section depicts the means for connecting suction tubing may be any convenient fitting but is preferably an angled suction tubing connector 48 having a tubular portion 60 and an integrally molded resilient catch 62 in at least one location that is matingly receivable on a land 64 formed into the upper edge of the skirt 36 at a plurality of locations. The tubular portion of the suction tubing connector can extend into fluid evacuation wells 66 that are formed to receive the suction tubing connector 48 with the inlet 68 proximate the lowermost portion of the wetted area of the base. The fluid evacuation wells 66 may be any convenient number, four are illustrated in the present embodiment but normally only one suction connector 48 is used. A peripheral fluid channel 30 receives fluids that run from any point within the peripheral wall 32 and conveys those fluids to the evacuation wells 66. Suction at one evacuation well 66 removes all fluid with the exception of a residual amount that is typically less than 75 ml for the complete apparatus, including an attached drape 52.

The base 22 raised center portion 26 may be supported by a post 70 of solid or resilient material to prevent accidental inversion of the slope of the channels 28 in the event that the fluid control island is stepped upon or run over by the wheel of an instrument cart.

FIG. 4 shows the suction tubing connector 48 in greater detail mated on a land 64 with the bottom peripheral surface 72 adjacent the distal edge 40 of the base 22 in contact with the floor 74. The bottom surface 76 of the evacuation wells 66 may also contact the floor 74.

FIG. 5 shows a detail of the peripheral wall 32 and the peripheral channel 30 for fluid evacuation. The drape 52 lower end 54 is attached to the base 22 conveniently at the peripheral wall 32 by adhesive, heat seal, sonic welding, or other suitable means, depending upon the properties of the materials from which the components are made. The splash pad 42 extends to proximity with the drape lower end 54 and may be affixed to the center 26 or ribs 44 by any convenient method. In some instances, anti-skid materials may be applied to the bottom surface 72.

An optional generally peripheral suction tubing guide channel 78 can be set into or formed in the upper skirt surface 38 interposed between the peripheral wall 32 and the distal edge 40. The tubing guide channel 78 may go all of the way around the base 22 or only part of the way. It is equivalently possible to attach other structures to the base to restrain suction tubing 50 from extending in undesired directions. If formed, the tubing guide channel 78 may be equipped with protrusions or nibs 80 for restraining the suction tubing 50 within the channel. It is also possible to form one or more generally planar tubing retainer members 82 resiliently disposed over the suction tubing guide channel 78. Fitting a flap, hinge, cover, or other structure over the suction tubing guide channel 78 to confine the tubing 50 in the channel can keep the work area neater and prevent accidental disconnection of suction from the base 22. If the base 22 is made of a resilient material, it can be a simple matter to sonic weld a plate 82 of the same material over the channel 78 so that the suction tubing 50 may be easily placed into the channel 78 and remain there until intentionally removed.

FIG. 6 presents alternative embodiments to the article shown in FIG. 1. The disposable surgical and diagnostic fluid control island 20 may optionally include a pre-attached surgical drape 52. That drape may include a tissue and debris capturing strainer pocket 84 with a drain 86 for the convenient collection of specimens that might require laboratory analysis. It may desirable to form the strainer pocket 84 integrally with the drape 52, however, it will be preferable in some cases to apply the pocket 84 after the patient is in position. The edges 88 of the upper end of the drape 56 that contact the patient may be fitted with a resilient member 90 such as foam either on the table-contacting side of the drape or inside a folded-over edge 88 segment. The resilient member 90 can raise the drape sufficiently to form a dam to prevent fluid from dispersing beneath the patient or along the patient's sides toward the head of the patient. Some surgical positions elevate the patient's buttocks during surgery which can cause fluids that impinge on the operating table to flow away from the fluid collection island. In those cases, especially, it can be helpful to take the additional step of fitting resilient fluid dispersal blocking members 90 between the patient contacting surface of the drape 52 and the operating table 58.

The fluid control island 20 and all of the alternative embodiments and all of their equivalents disclosed herein can comprise a component of a system for determining the fluid balance of patients, particularly with respect to distension media, but applicable to other fluids, as well. This island can also be used independently to remove fluids from orthopedic surgeries on smaller joints such as the hand, arm and shoulder.

This fluid control island 20 is also adapted for birthing and can be used to make clean-up quicker and easier after most surgical and endoscopic diagnostic procedures. In applications such as birthing where quantification of fluid volume may not be required, the base 22 may be made deeper so that a larger volume of fluid can be retained and a lower evacuation rate can be adequate to remove fluid flow rate surges without exceeding the volumetric capacity of the apparatus. Fluid flow surges, inherent in some procedures, can also result from instrument flushing, cleanup, connection failure, and other causes. By routing all fluid flow to the disposable surgical and diagnostic fluid control island 20 and quantitatively recovering those fluids, those conditions and events do not become sources of uncertainty.

Changes and modifications in the specifically described embodiments can be carried out without departing from the scope of the invention which is intended to be limited only by the scope of the appended claims.

TABLE 1

ESTIMATES OF FLUID VOLUMES-SIMULATED OPERATING ROOM CONDITIONS

| Actual Volume (ml) | Nurse 1 estimate (ml) | Nurse 2 estimate (ml) | Nurse 3 estimate (ml) | Nurse 4 estimate (ml) | Mean of estimates (ml) | Mean of estimate errors (%) | Mean of estimate errors (ml) | Largest error (ml) | Smallest error (ml) |
|---|---|---|---|---|---|---|---|---|---|
| FLUID REMAINING IN 3 LITER BAGS | | | | | | | | | |
| 2879 | 2460 | 2480 | 2500 | 2500 | 2485 | −14% | −394 | −419 | −379 |
| 1546 | 1200 | 1300 | 1350 | 1200 | 1263 | −18% | −284 | −346 | −196 |
| 2244 | 1800 | 1950 | 1800 | 1900 | 1863 | −17% | −382 | −444 | −294 |
| 1784 | 1550 | 1600 | 1800 | 1700 | 1663 | −7% | −122 | −234 | 16 |
| 843 | 525 | 575 | 600 | 500 | 550 | −35% | −293 | −343 | −243 |
| 1714 | 1525 | 1500 | 1500 | 1500 | 1506 | −12% | −208 | −214 | −189 |
| 1075 | 900 | 875 | 900 | 900 | 894 | −17% | −181 | −200 | −175 |
| 597 | 275 | 275 | 250 | 300 | 275 | −54% | −322 | −347 | −297 |
| 770 | 450 | 450 | 450 | 400 | 438 | −43% | −333 | −370 | −320 |
| 3114 | 2710 | 2800 | 3250 | 3000 | 2940 | −6% | −174 | −404 | −114 |
| FLUID IN KICK BUCKETS | | | | | | | | | |
| 770 | 250 | 400 | 650 | 500 | 450 | −42% | −320 | −520 | −120 |
| 1546 | 600 | 1200 | 1100 | 1000 | 975 | −37% | −571 | −948 | −346 |
| 1075 | 800 | 1000 | 900 | 1000 | 925 | −14% | −150 | −275 | −75 |
| 821 | 400 | 500 | 600 | 500 | 500 | −39% | −321 | −421 | −221 |
| FLUID ON OPERATING ROOM FLOOR | | | | | | | | | |
| 570 | 150 | 300 | 200 | 200 | 213 | −63% | −358 | −420 | −270 |
| 282 | 100 | 200 | 100 | 100 | 125 | −56% | −157 | −182 | −82 |
| 642 | 150 | 400 | 125 | 200 | 219 | −66% | −423 | −517 | −242 |
| 1115 | 300 | 600 | 275 | 300 | 369 | −67% | −746 | −840 | −515 |
| 381 | 100 | 250 | 140 | 100 | 148 | −61% | −234 | −281 | −131 |

DRAWING REFERENCE NUMBERS 20 disposable fluid control island
22 impermeable vessel-forming base or bottom portion
23 upper surface
24 undersurface
26 raised center
28 sloping channels
30 peripheral channel
32 peripheral wall
34 fluid-contacting portion or wetted area
36 skirt
38 upper skirt surface
40 distal base edge
42 splash pad
44 rib
46 means for connecting suction tubing
48 suction tubing connector
50 suction tubing
52 drape
54 drape lower end
56 drape upper end
58 operating table
60 tubular portion
62 resilient catch
64 land
66 evacuation well
68 suction inlet
70 center post
72 bottom peripheral surface of base
74 floor
76 bottom surface of evacuation well
78 suction tubing guide channel
80 protrusions or nibs
82 tubing retainer member
84 tissue and debris strainer pocket
86 strainer pocket drain openings
88 patient contacting drape edges
90 resilient members

What is claimed is:

1. A disposable surgical and diagnostic fluid control island placeable on an operating room floor for selectably collecting, retaining and draining fluids received from patients during surgery comprising:
 a. a generally broad, shallow, impermeable vessel-forming base having
  i. a peripherally floor-contacting, undersurface portion and an upper surface portion with a raised center,
  ii. a multiplicity of sloping channels extending downward from the raised center toward a lower peripheral channel at the base of a generally vertical peripheral wall disposed between a fluid-contacting central portion and a distal peripheral skirt,
  iii. a generally beveled upper skirt surface extending between the top of the generally vertical peripheral wall and a distal base edge proximate the floor,
 b. a generally non-absorbent splash pad disposed within the fluid-contacting central portion and supported by ribs above the sloping channels and extending proximal to the raised peripheral wall, and
 c. means for connecting fluid-removing suction tubing proximate the lower peripheral channel.

2. The disposable surgical and diagnostic fluid control island defined in claim 1 wherein an elongated drape lower end is affixed to the base proximate the peripheral wall and an elongated drape upper end may be disposed upon an operating table for fluid communication between a patient and the base.

3. The disposable surgical and diagnostic fluid control island defined in claim 2 wherein the means for connecting suction tubing is further comprised of a tubular portion and a catch portion, the catch portion being adapted for being affixed proximate the top of the peripheral wall.

4. The disposable surgical and diagnostic fluid control island defined in claim 3 being further comprised of a generally peripheral suction tubing guide channel set into the upper skirt surface interposed between the peripheral wall and the distal edge.

5. The disposable surgical and diagnostic fluid control island defined in claim 4 wherein the suction tubing guide channel is further comprised of tubing retaining nibs.

6. The disposable surgical and diagnostic fluid control island defined in claim 4 being further comprised of a generally planar tubing retainer member resiliently disposed over the suction tubing guide channel.

7. The disposable surgical and diagnostic fluid control island defined in claim 2 being further comprised of a generally peripheral suction tubing guide channel set into the upper skirt surface interposed between the peripheral wall and the distal edge.

8. The disposable surgical and diagnostic fluid control island defined in claim 7 being further comprised of a generally planar tubing retainer member resiliently disposed over the suction tubing guide channel.

9. The disposable surgical and diagnostic fluid control island defined in claim 8 being further comprised of drape-raising resilient members set into the drape upper end.

10. A method for selectably collecting, retaining and draining fluids received from patients during surgery in a disposable surgical and diagnostic fluid control island placeable on an operating room floor comprising the steps of:
   a. placing onto an operating room floor a generally broad, shallow, impermeable vessel-forming base having
      i. a generally horizontal, peripherally floor-contacting, undersurface portion,
      ii. an upper surface portion having a raised center having sloping channels extending downwardly from the center toward a lower peripheral channel at the base of a generally vertical peripheral wall disposed between a fluid-contacting central portion and a radially outwardly disposed skirt,
      iii. a generally beveled upper skirt surface extending between the top of the generally vertical peripheral wall and a distal base edge proximate the floor,
   b. attaching a generally non-absorbent splash pad disposed within the fluid-contacting central portion of the base and supporting the splash pad above the sloping fluid conducting channels that extend proximal to the raised peripheral wall, and
   c. connecting fluid-removing suction tubing to the base proximate the lower peripheral channel.

11. The method of claim 10 further comprising the steps of affixing an elongated drape lower end to the base proximate the peripheral wall and positioning an elongated drape upper end upon an operating table proximate a patient for fluid communication between the patient and the base fluid-contacting central portion.

12. The method of claim 11 further comprising the step of fitting resilient fluid dispersal blocking members between the patient contacting surface of the drape and the operating table.

13. The method of claim 12 further comprising the step of forming a peripheral suction tubing guide channel.

14. The method of claim 13 further comprising the step of affixing a resiliently displaceable tubing retainer member over the suction tubing guide channel.

15. A method of making a disposable surgical and diagnostic fluid control island placeable on an operating room floor for selectably collecting, retaining and draining fluids received from patients during surgery comprising the steps of:
   a. forming a generally broad, shallow, impermeable vessel-forming base having
      i. a generally horizontal, peripherally floor-contacting, undersurface portion,
      ii. an upper surface portion with a raised center having sloping channels that extend from the raised center downwardly toward a lower peripheral channel at the base of a generally vertical peripheral wall disposed between a fluid-contacting central portion and a peripheral skirt,
      iii. a generally beveled upper skirt surface extending between the top of the generally vertical peripheral wall and a distal base edge proximate the floor,
   b. affixing to the base raised center a generally non-absorbent splash pad disposed within the fluid-contacting central portion and supporting the splash pad on ribs disposed above the radial sloping channels and extending proximal to the raised peripheral wall, and
   c. connecting fluid-removing suction tubing proximate the lower peripheral channel.

16. The method of claim 15 further comprising the steps of affixing a lower end of an elongated drape to the base proximate the peripheral wall and disposing an elongated drape upper end upon an operating table for fluid communication between a patient and the base.

17. The method of claim 16 further comprising the step of fitting resilient fluid dispersal blocking members between the patient contacting surface of the drape and the operating table.

18. The method of claim 17 further comprising the steps of connecting suction tubing to the base using a connector having a tubular portion and a catch portion, the catch portion being adapted for being affixed proximate the top of the peripheral wall.

19. The method of claim 18 further comprising the step of forming a peripheral suction tubing guide channel.

20. The method of claim 19 further comprising the step of affixing a resiliently displaceable tubing retainer member over the suction tubing guide channel.

\* \* \* \* \*